United States Patent [19]

Taniguchi et al.

[11] Patent Number: 4,684,732

[45] Date of Patent: Aug. 4, 1987

[54] PROCESS FOR PREPARATION OF PHTHALIDE DERIVATIVES

[75] Inventors: Masao Taniguchi, Machida; Yoshiharu Morita; Shuzo Hayakawa, both of Yokohama; Osamu Kawashima, Kitakyushu, all of Japan

[73] Assignee: Mitsubishi Chemical Industries Limited, Tokyo, Japan

[21] Appl. No.: 708,811

[22] Filed: Mar. 5, 1985

[51] Int. Cl.$^4$ .................. C07D 405/04; C07D 405/14
[52] U.S. Cl. ..................................... 546/144; 546/90; 546/147
[58] Field of Search ............... 546/144, 147, 90

[56] References Cited

U.S. PATENT DOCUMENTS 3,989,704 11/1976 Houlihan et al. .................. 546/144
4,175,191 11/1979 Houlihan et al. .................. 546/144

FOREIGN PATENT DOCUMENTS 873935 8/1961 United Kingdom .

Primary Examiner—Richard L. Raymond
Assistant Examiner—James H. Turnipseed
Attorney, Agent, or Firm—Cushman, Darby & Cushman

[57] ABSTRACT

Disclosed herein is a process for preparing phthalide derivatives represented by the general formula (IV):

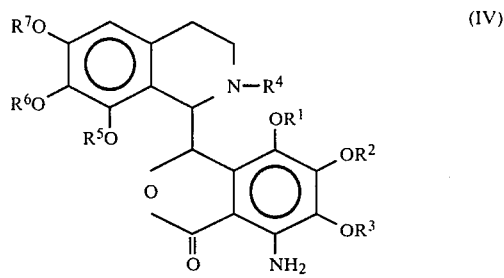

wherein $R^1$ to $R^7$ are herein defined, comprising (i) reacting a nitrophthalide of the general formula (I) defined herein with an isoquinoline of the general formula (II) defined herein, and (ii) reducing the resultant phthalideisoquinoline of the general formula (III) defined herein. The process is characterized in (A) that the reaction defined in (i) is carried out in methanol, and/or (B) that the nitrophthalide of the general formula (I) is a nitrophthalide obtained by a reaction of a phthalide of the general formula (V) defined herein with copper nitrate or zinc nitrate.

7 Claims, No Drawings 4,684,732

PROCESS FOR PREPARATION OF PHTHALIDE DERIVATIVES

Field of the Invention

This invention relates to a process for preparing phthalide derivatives.

BACKGROUND OF THE INVENTION

Phthalide derivatives represented by the general formula (IV):

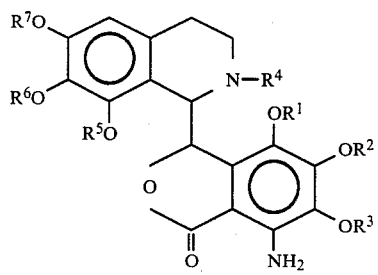

wherein $R^1$ to $R^7$ are independently selected from lower alkyl groups, and either $R^5$ and $R^6$ or $R^6$ and $R^7$ may otherwise form together with each other a methylene group, for example tritoqualine, have been used as an antiallergic agent.

Generally, the phthalide derivatives of the general formula (IV) may be prepared by the reaction of nitrophthalides represented by the general formula (I):

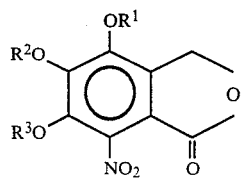

wherein $R^1$ to $R^3$ are as defined above, with isoquinolines represented by the general formula (II):

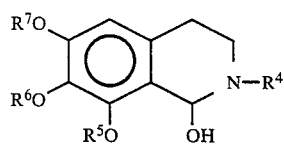

wherein $R^4$ to $R^7$ are as defined above, to produce phthalideisoquinolines represented by the general formula (III):

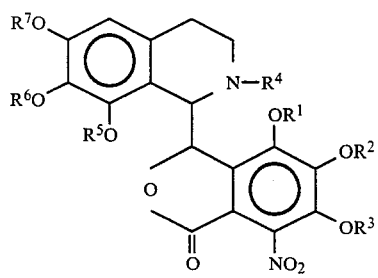

wherein $R^1$ to $R^7$ are as defined above, followed by reduction of the phthalideisoquinolines.

The nitrophthalides of the general formula (I) have hitherto been prepared by reacting phthalides represented by the general formula (V):

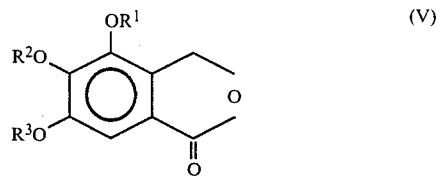

wherein $R^1$ to $R^3$ are as defined above with fuming nitric acid: see British Pat. No. 873,935. In this process, however, a satisfactory yield has not always been attained On the other hand, the reaction of the nitrophthalides of the general formula (I) with the isoquinolines of the general formula (II) for producing the phthalideisoquinolines of the general formula (III) has been carried out in ethanol, as shown in British Pat. No. 873,935. In this process, also, only unsatisfactory yield is usually obtained.

The present inventors have made great efforts to improve the yields of these reactions and now found that the use of nitrate salts of specified metals in the reaction of the phthalides of the general formula (V) and the use of methanol in the reaction of the nitrophthalides of the general formula (I) with the isoquinolines of the general formula (II) give markedly good results, which have led us to the present invention.

SUMMARY OF THE INVENTION

This invention provides a process for preparing phthalide derivatives of the general formula (IV), which comprises:

(i) reacting a nitrophthalide of the general formula (I) with an isoquinoline of the general formula (II) to produce a phthalideisoquinoline of the general formula (III), and (ii) reducing the phthalideisoquinoline. The process is characterized in:

(A) that the reaction (i) is carried out in methanol; and/or (B) that the nitrophthalide of the general formula (I) used in the reaction (i) is prepared by reacting a phthalide of the general formula (V) with copper nitrate or zinc nitrate.

DESCRIPTION OF THE INVENTION

The invention will hereinafter be described in detail.

In the general formulae (I) to (V), $R^1$ to $R^7$ represent same or different lower alkyl groups having 1 to 6 carbon atoms, such as methyl, ethyl, n-propyl, iso-propyl, n-butyl and the like. Either $R^5$ and $R^6$ or $R^6$ and $R^7$ in the formulae (II) to (IV) may together form a methylene group: that is, either $OR^5$ and $OR^6$ or $OR^6$ and $OR^7$ may together form methylenedioxy group.

In order to prepare tritoqualine, for example, the nitrophthalide of the general formula (I) wherein $R^1$ to $R^3$ are all ethyl groups is chosen and cotarnine having the following formula:

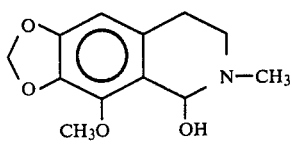

is used as an isoquinoline of the general formula (II).

(A). In the process of the invention, the reaction of the nitrophthalides of the general formula (I) with the isoquinolines of the general formula (II), namely the reaction (i), may preferably be carried out in methanol.

The amount of methanol used may be 1.5–10 times by volume, preferably 2.5–3 times by volume, based on the amount of the nitrophthalide used.

The isoquinoline of the general formula (II) may usually be used in an approximately equimolar amount to the nitrophthalide.

The reaction (i) may be carried out at a temperature of 50–80° C. for a period in the range of 8–36 hours.

After completion of the reaction (i), the phthalideisoquinoline produced may be purified in a conventional manner.

(B). The nitrophthalides of the general formula (I) used in the reaction (i) in the process of this invention may preferably be those obtained by the reaction of phthalides of the general formula (V) with copper or zinc nitrate.

The reaction of the phthalides with the nitrate is usually carried out in a solvent, such as acetic acid, acetic anhydride, trifluoroacetic acid, trifuloroacetic anhydride, propionic anhydride and the like. Acetic anhydride is especially preferred.

The copper or zinc nitrate may be used in an amount of 0.8–5 times by mole, preferably 1.0–1.5 times by mole, based on the phthalide (V).

The amount of the solvent used may be in the range of 3–20 times by volume, preferably 4–5 times by volume, based on the phthalide (V).

The reaction is carried out at a temperature in the range of 0–120° C., preferably 10–25° C.

There can be utilized, of course, both copper nitrate and zinc nitrate in the reaction.

Preferably, copper nitrate or zinc nitrate is gradually added to a mixture of the phthalide and solvent to avoid generating heat excessively in the reaction. Generally, the nitrate is added in a time period of 0.5–24 hours and the reaction may be allowed to proceed for 1–16 hours, preferably 2–4 hours.

In order to further improve the yield of the product, i.e., the nitrophthalide of the general formula (I), in the process of the invention, both the phthalide (V) and the nitrate as a nitrating agent can be simultaneously supplied gradually to the above-mentioned solvent.

The phthalide (V) is supplied in such a rate that the concentration of unreacted phthalide in the solvent may be adjusted to 4% by weight or less, preferably 0.1–3% by weight. Too high supply rate will cause more side-reactions.

On the other hand, the supply rate of the nitrating agent is adjusted such that its concentration in the solvent may be in the range of 2 times by mole or less, preferably 0.5–1.5 times by mole, based on the unreacted phthalide. With a too high rate, unstable nitrating agents may accumulate in the reaction system and cause a problem of safety.

Generally, the phthalide and the nitrating agent are supplied in the form of solid, while they can be in the form of a solution or slurry in the above-mentioned solvent, or a diluent or the like. They may be supplied either continuously or intermittently.

After the reaction the product nitrophthalide (I) may be purified in any conventional manner.

Generally, the product may be recovered by adding water to the reaction mixture after reaction, filtering out the deposited crystal and washing it with water. If necessary, the product may preferably be recrystallized from a solvent, such as methanol, to further purify.

In the process of the invention, the phthalideisoquinoline of the general formula (III) obtained in the reaction (i) may be subjected to the reduction reaction to produce the phthalide derivative of the general formula (IV).

The reduction reaction may usually be carried out at a temperature in the range of from -20° C., preferably from 10 to 25° C., for a period in the range of from 0.5 to 24 hours in a solvent such as glacial acetic acid, tetrahydrofuran and acetone. Stannous chloride-hydrochloric acid, tinhydrochloric acid, iron-hydrochloric acid, etc. may be utilized in the reduction.

According to the process of this invention, the end product phthalide derivatives can be obtained with an improved yield.

Further, the obtained phthalide derivatives substantially have the configuration of 1RS-3'RS, that is, the same configuration as tritoqualine, and therefore, the process of the invention is very useful industrially.

DESCRIPTION OF THE PREFERRED EMBODIMENTS

The invention will be more fully illustrated with the following non-limiting examples.

EXAMPLE 1 Preparation of 4,5,6-triethoxy-7-nitrophthalide

Acetic anhydride (200 ml) was added to 53.2 g (0.20 mole) of 4,5,6-triethoxyphthalide. A reaction vessel containing the mixture was placed on a water bath of 10–15° C., and then 58.1 g (0.24 mole) of cupric nitrate trihydrate was gradually added to the mixture under rigorously stirring while maintaining the temperature of the reaction mixture at 10°–25° C. After completion of the addition of cupric nitrate, the reaction mixture was stirred at 10°–25° C. for 3 hours and gradually poured into 600 g of ice water. After stirring at room temperature for one hour, the deposited crystal was filtered out and thoroughly washed with water. The crystal was dissolved into 250 ml of methanol by heating to 40° C. and the undissolved residue was filtered out. Methanol (200 ml) was distilled off under reduced pressure and 25 ml of water was then added to the remaining solution. The deposited crystal was filtered out and dried. Thus, 41.6 g of 4,5,6-triethoxy-7-nitrophthalide having a melting point of 85.5–87° C. was obtained with a yield of 67%.

EXAMPLE 2

The procedures of Example 1 were repeated except that cupric nitrate trihydrate was replaced by zinc nitrate hexahydrate. There was obtained 4,5,6-triethoxy-7-nitrophthalide with a yield of an approximately 50%.

COMPARATIVE EXAMPLE 1 Preparation of 4,5,6-triethoxy-7-nitrophthalide

Glacial acetic acid (14 ml) was added to 5.32 g (0.02 mole) of 4,5,6-triethoxyphthalide. Into the reaction mixture on a water bath at 30–35° C., 14 ml of fuming nitric acid, d=1.52, was gradually added dropwise over a time period of 9 hours. After completion of the addition, the reaction mixture was allowed to stand overnight at room temperature and thereafter 80 ml of water was added to deposit crystals. The crystals were filtered out, washed thoroughly with water and dried. There was obtained 2.20 g of 4,5,6-triethoxy-7-nitrophthalide having a melting point of 82.5–84.5° C. with a yield of 35%.

EXAMPLE 3 Preparation of 4,5,6-triethoxy-7-nitrophthalide

To 102 g of acetic anhydride, 26.6 g (0.10 mole) of 4,5,6-triethoxyphthalide and 33.8 g (0.14 mole) of cupric nitrate trihydrate were added uniformly in a substantially constant rate over a period of one hour while maintaining the temperature of the reaction mixture at 30° C. under stirring. The concentration of unreacted 4,5,6-triethoxyphthalide in the reaction mixture was maintained at approximately 2% by weight during the addition period.

After the addition period, the reaction mixture was stirred at 30° C. for an additional one hour, released into 400 g of ice water and further stirred at room temperature for one hour. The deposited crystal was filtered out, washed thoroughly with water and dissolved into 150 ml of methanol with heating at 40° C. After subjecting the solution to filtration to remove undissolved residues, 120 ml of methanol was distilled off under reduced pressure from the filtrate. Fifteen ml of water was added to the remaining solution and the deposited crystal was filtered out and dried. There was obtained 23.7 g of 4,5,6-triethoxy-7-nitrophthalide with a yield of 76%.

EXAMPLE 4

The procedures of Example 3 were repeated except that 33.8 g (0.14 mole) of cupric nitrate trihydrate was replaced by 41.6 g (0.14 mole) of zinc nitrate hexahydrate. There was obtained 18.4 g of 4,5,6-triethoxy-7-nitrophthalide with a yield of 59%.

EXAMPLE 5 Preparation of 2-methyl-6,7-methylenedioxy-8-methoxy-1-[4,5,6-triethoxy-7-nitrophthalidyl-(3)]-1,2,3,4-tetrahydroisoquinoline A reaction of 88 ml of methanol added to 34.2 g (0.11 mole) of 4,5,6-triethoxy-7-nitrophthalide and 26.1 g (0.11 mole) of cotarnine was conducted under stirring for 10 hours in an oil bath heated at 80° C. The reaction mixture was allowed to cool to room temperature. After adding 176 ml of methanol and 66 ml of methyl isobutyl ketone to the mixture at room temperature, the mixture was stirred for one hour. The resulting crystal was filtered out and washed with a small amount of methanol. The product having a melting point of 149.5–151.5° C. was obtained in an amount of 37.0 g with a yield of 64%.

The filtrate and washings were combined and concentrated under reduced pressure. There were further added 5.2 g (0.022 mole) of cotarnine and 18 ml of methanol to the remaining oily components, which were then allowed to react for 10 hours and post-treated in the same manner as above. The product was obtained in an amount of 9.4 g with a yield of 16%. All the products were in the form of 1RS-3'RS epimer.

COMPARATIVE EXAMPLE 2

After adding 30 ml of anhydrous ethanol to 2.10 g (8.86 m mole) of 4,5,6-triethoxy-7-nitrophthalide, 2.75 g (8.84 m mole) of cotarnine and 2.10 g of powdery, anhydrous sodium sulfate, the mixture was refluxed with stirring under nitrogen flow for 27 hours. After the reaction, the mixture was allowed to stand overnight in a refrigerator and the deposited crystal was filtered out and dried. There were obtained 1.76 g of 2-methyl-6,7-methylenedioxy-8-methoxy-   1-[4,5,6-triethoxy-7-nitrophthalidyl-(3)]-1,2,3,4-tetrahydro-isoquinoline having a melting point of 124°–141° C. with a yield of 36%. The productr consisted of 1RS-3'RS epimer and IRS-3'SR epimer in a proportion of approximately 2.5 : 1.

EXAMPLE 6 Preparation of tritoqualine

After adding 100 ml of acetone to 26.5 g (0.05 mole) of (1RS,3'RS)-2-methyl-6,7-methylenedioxy-8-methoxy-1-[4,5,6-triethoxy-7-nitrophthalidyl-(3)]-1,2,3,4-tetrahydroisoquinoline and 11.9 g (0.10 mole) of tin powder, 117 ml of 8N aqueous hydrochloric acid solution was gradually added dropwise under stirring over a period of 1.5 hours while cooling with ice. The addition rate was adjusted in such a manner that the temperature of the reaction mixture should not exceed 20° C.

After completion of the addition the ice bath was removed. The reaction mixture was stirred to react at room temperature for one hour. After acetone was distilled off under reduced pressure, the remaining solution was extracted with dichloroethane. To the combined dichloroethane layers, 150 ml of 10% aqueous sodium hydroxide solution was gradually added while cooling in an ice bath to render the amine compounds in the free form. After removing the water layer, the dichloroethane layer was washed twice with 1% aqueous EDTA solution and then with water, and dried on magnesium sulfate. The solvent was distilled off and the residual crystal was recrystallized from methyl ethyl ketone. There was obtained 23.0 g of pure tritoqualine having a melting point of 180.5°–182° C. with a yield of 92%.

What is claimed is:

1. A process for preparing phthalide derivatives represented by the general formula (IV):

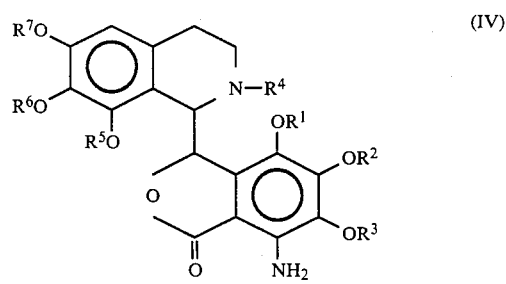

wherein $R^1$ to $R^7$ are independently selected from lower alkyl groups and either $R^5$ and $R^6$ or $R^6$ and $R^7$ may otherwise together form a methylene group, comprising:

(i) reacting in a solvent a phthalide represented by the general formula (V):

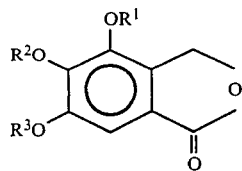

wherein $R^1$ to $R^3$ are as defined above, with copper nitrate or zinc nitrate to obtain a nitrophthalide;

(ii) reaching the nitrophthalide with isoquinoline represented by the general formula (II):

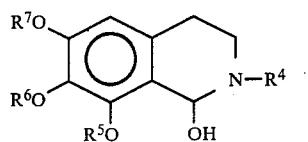

wherein $R^4$ to $R^7$ are as defined above, in methanol in an amount of 1.5 to 10 times by volume of nitrophthalide and a reaction temperature of 50° to 80° C. for a reaction period of 8 to 36 hours to produce a phthalide isoquinoline represented by the general formula (III):

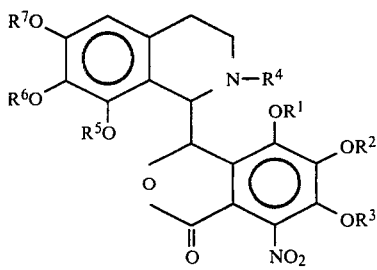

wherein $R^1$ to $R^7$ are as defined above; and (iii) reducing the phthalideisoquinoline in a solvent at a reaction temperature of −20° to 120° C. and reaction period of 0.5 to 24 hours.

2. The process of claim 1, wherein the solvent in step (i) is acetic anhydride.

3. The process of claim 1, wherein the amount of copper nitrate or zinc nitrate used is 0.8–5 times by mole, based on the phthalide used.

4. The process of claim 2, wherein the amount of the solvent used is 3–20 times by volume based on the phthalide used.

5. The process of claim 1, wherein both the phthalide and copper nitrate or zinc nitrate are gradually added to the solvent.

6. The process of claim 5, wherein the phthalide is supplied in such a rate that the concentration of unreacted phthalide in the solvent is 4% by weight or less.

7. The process of claim 5, wherein copper nitrate or zinc nitrate is supplied in such a rate that the concentration thereof in the solvent is 2 times by mole or less, based on the unreacted phthalide.

* * * * *